(12) United States Patent
Watanabe et al.

(10) Patent No.: US 8,697,100 B2
(45) Date of Patent: Apr. 15, 2014

(54) SURFACE-TREATED POWDER AND A METHOD OF PRODUCING IT, AND COSMETICS COMPRISING THE SURFACE-TREATED POWDER

(75) Inventors: Yuhya Watanabe, Tokyo (JP); Ikko Tanaka, Tokyo (JP)

(73) Assignees: Nikko Chemicals Co., Ltd., Tokyo (JP); Cosmos Technical Center Co., Ltd., Tokyo (JP)

( * ) Notice: Subject to any disclaimer, the term of this patent is extended or adjusted under 35 U.S.C. 154(b) by 0 days.

(21) Appl. No.: 13/356,253

(22) Filed: Jan. 23, 2012

(65) Prior Publication Data

US 2013/0189331 A1 Jul. 25, 2013

(51) Int. Cl.
*A61K 8/02* (2006.01)
*B05D 7/00* (2006.01)

(52) U.S. Cl.
USPC .......................................... 424/401; 427/222

(58) Field of Classification Search
USPC .......................................... 424/401; 427/222
See application file for complete search history.

(56) References Cited

U.S. PATENT DOCUMENTS

2011/0110995 A1* 5/2011 Hasegawa et al. ............ 424/401
2012/0039971 A1* 2/2012 Kaneko et al. ................ 424/401

FOREIGN PATENT DOCUMENTS

| JP | 07-112915 A | | 5/1995 |
|---|---|---|---|
| JP | 11-322542 A | * | 11/1999 |
| JP | 2000-128737 A | | 5/2000 |
| JP | 2000-309509 A | | 11/2000 |
| JP | 2003-104842 A | * | 4/2003 |
| JP | 2008-214229 A | | 9/2008 |
| JP | 2009-269866 A | | 11/2009 |
| JP | 2010-121099 A | * | 6/2010 |

* cited by examiner

*Primary Examiner* — Blessing M Fubara
(74) *Attorney, Agent, or Firm* — Lucas & Mercanti, LLP

(57) ABSTRACT

The objects of the present invention are to provide a surface-treated powder that is excellent in water repellency and oil repellency and provides smooth texture and good adhesion when applied to skin, to produce the surface-treated powder simply and inexpensively, and to provide cosmetics comprising the surface-treated powder. Specifically, according to the present invention, a surface-treated powder wherein the surface of a material powder is treated with perfluoropolyether-phosphate represented by general formula (1) and an anionic polymer having a perfluoropolyether chain, which is represented by general formula (2), or perfluoropolyetherphosphate represented by general formula (1) and a cationic polymer having a perfluoropolyether chain, which is represented by general formula (3), and cosmetics comprising the surface-treated powder are provided.

9 Claims, No Drawings

SURFACE-TREATED POWDER AND A METHOD OF PRODUCING IT, AND COSMETICS COMPRISING THE SURFACE-TREATED POWDER

FIELD OF THE INVENTION

The present invention relates to a surface-treated powder, which has excellent water repellency, oil repellency, and the smooth texture; and cosmetics in which the powder is included.

BACKGROUND OF THE INVENTION

Various powders are used as powders for cosmetics such as makeup cosmetics, sunscreen cosmetics, mascara, nail enamel, and lipstick. There have been many investigations of surface treatment conducted with the aim of providing water repellency and oil repellency for different purposes. Such purposes include preventing makeup from wearing off due to sweat, tears, rain, outdoor sports, and swimming in the sea, and preventing color transfer to clothes, drinking vessels, and the like. Examples of methods that have been proposed include a method using a silica-coated powder, a method using a powder subjected to surface treatment with various silicone derivatives, and a method using a powder with water repellency and oil repellency, which is prepared by surface treatment with a surface treatment agent having a perfluoro group.

Regarding powder subjected to surface treatment with a surface treatment agent having a perfluoroalkyl group, a method that involves treatment with perfluoroalkylphosphate is known (patent document 1). However, powders treated with perfluoroalkylphosphate are difficult to apply properly, powdery, and adhere poorly to skin. For such reasons, a method using a powder treated with a combination of perfluoroalkylphosphate and another surface treatment agent has been proposed (patent document 2). However, a specific perfluoroalkyl group presents safety concerns. Hence, a surface treatment agent for powder has been required as an alternative to a surface treatment agent having such specific perfluoroalkyl group.

A surface treatment agent having a perfluoropolyether chain has been examined as a means to address the problem. As powders treated with a surface treatment agent having a perfluoropolyether chain, a powder treated with perfluoropolyetherphosphate ester and cosmetics comprising the same have been reported (patent documents 3 and 4). As a powder treated with a silane compound having a perfluoropolyether chain, a powder treated with a perfluoropolyether-modified amino silane compound has been reported (patent document 5). An anionic polymer containing perfluoropolyether has further been reported (patent document 6). However, these powders using such surface treatment agents are insufficient in terms of water repellency, oil repellency, and the like, and are also not satisfactory in terms of adhesiveness or texture. Also, a surface-treated powder produced with a surface treatment agent that enables simple and inexpensive forms of surface treatment has also been desired.

Patent document 1 JP Patent Publication (Kokai) No. 7-112915 A (1995)
Patent document 2 JP Patent Publication (Kokai) No. 2009-269866 A
Patent document 3 JP Patent Publication (Kokai) No. 2000-128737 A
Patent document 4 JP Patent Publication (Kokai) No. 2000-309509 A
Patent document 5 JP Patent Publication (Kokai) No. 2008-214229 A
Patent document 6 JP Patent Publication (Kokai) No. 2010-121099 A

SUMMARY OF THE INVENTION

The objects of the present invention are to provide a surface-treated powder that is excellent in water repellency and oil repellency and provides a smooth texture and good adhesion when applied to skin, to produce the surface-treated powder simply and inexpensively, and to produce cosmetics comprising the surface-treated powder.

As a result of intensive studies to achieve such objects, the present inventors have discovered that synergistic effects can be obtained in terms of water repellency, oil repellency, adhesiveness, and texture through surface treatment of a material powder with a combination of perfluoropolyetherphosphate represented by general formula (1) and an anionic polymer having a perfluoropolyether chain, which is represented by general formula (2), or a cationic polymer having a perfluoropolyether chain, which is represented by general formula (3). The present inventors have further discovered that cosmetics can be obtained with the use of the surface-treated powder of the present invention that do not easily result in makeup wearing off due to sweat or sebum and provide a smooth texture and good adhesion when applied to skin. Thus, the present inventors have completed the present invention.

According to the present invention, a surface-treated powder that is excellent in water repellency, oil repellency, provides a smooth texture and good adhesion when applied to skin. Unlike conventional water repellent and oil repellent powders, the surface-treated powder of the present invention is also excellent in terms of its miscibility with various powders to be used for cosmetics, so that highly functional cosmetics that provide a good texture can be easily achieved. Specifically, examples of cosmetics that can be provided herein include make-up cosmetics that do not easily result in makeup wearing off due to sweat or water, UV protective cosmetics, and cosmetics such as lipstick and foundation that do not easily result in color transfer to drinking vessels, clothes, or the like.

DETAILED DESCRIPTION OF THE PREFERRED EMBODIMENTS

The surface-treated powder of the present invention will be described in detail below.

The present invention provides a surface-treated powder, wherein the surface of a material powder is treated with a combination of surface treatment components:
perfluoropolyetherphosphate represented by general formula (1)

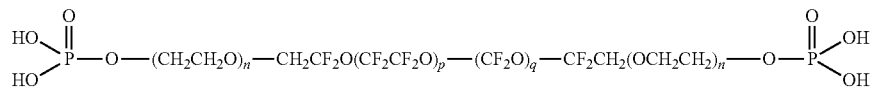

(wherein p denotes an integer between 1 and 50, q denotes an integer between 1 and 10, and n denotes an integer between 1 and 5); and an anionic polymer having a perfluoropolyether chain, which is represented by general formula (2)

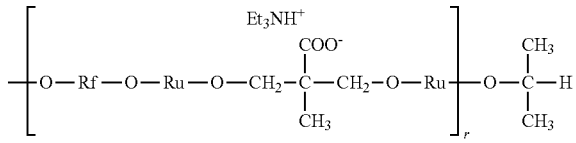

(wherein r denotes an integer between 1 and 50, Rf denotes general formula (4), and Ru denotes general formula (5)) or a cationic polymer having a perfluoropolyether chain, which is represented by general formula (3);

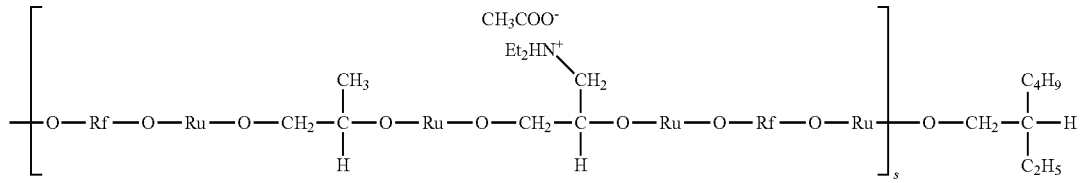

(wherein s denotes an integer between 1 and 50, Rf denotes general formula (4), and Ru denotes general formula (5)). Here, the expression, "the surface of a material powder was treated using surface treatment components" means that surface treatment components bound to the surface of the material powder, so that the surface of the material powder was coated with the surface treatment components.

Furthermore, Rf (perfluoropolyether part) in the anionic polymer having a perfluoropolyether chain, which is represented by general formula (2), and the cationic polymer having a perfluoropolyether chain, which is represented by general formula (3), is represented by general formula (4);

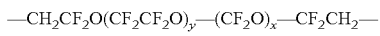

—CH$_2$CF$_2$O(CF$_2$CF$_2$O)$_y$—(CF$_2$O)$_x$—CF$_2$CH$_2$—

(wherein x denotes an integer between 1 and 100 and y denotes an integer between 1 and 100).

Ru (urethane bond part) in the anionic polymer having a perfluoropolyether chain, which is represented by general formula (2), and the cationic polymer having a perfluoropolyether chain, which is represented by general formula (3), is represented by general formula (5);

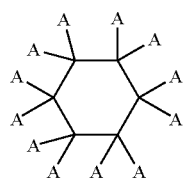

(wherein A is a functional group in cyclohexane, two of As are —NH—CO— or —CH$_2$—NH—CO— forming a urethane bond structure and two As are the same or different, and the other As denote arbitrarily hydrogens or methyl groups).

In the present invention, a powder is treated with a combination of the above surface treatment components, thereby synergistically improving the functions of the powder. Furthermore, as described in detail in the following Examples, when a powder is treated by a wet method (but the production method of a powder is not limited thereto), although the properties of a treatment agent to be used later (because of the order of treatment) tend to be exhibited stronger, a powder excellent in oil repellency, texture, adhesiveness, and further miscibility with another surface-treated powder, which cannot be obtained by conventional surface treatment, can be obtained. Furthermore, although the ratio of surface treatment components to a material powder or the amount of a combination thereof is not limited, the surface treatment components of the present invention range from 0.5 to 40 (0.5 or more and 40 or less) parts by mass, preferably range from 1 to 20 parts by mass, and further preferably range from 2 to 10 parts by mass with respect to 100 parts by mass of a material powder. Specifically, with respect to 100 parts by mass of the material powder, the amounts of the surface treatment agents to be coated range from 0.5 to 40 parts by mass, preferably range from 1 to 20 parts by mass, and further preferably range from 4 to 10 parts by mass.

Furthermore, the mass ratio of the surface treatment component(s) to a powder preferably ranges from 5/95 to 95/5, and further preferably ranges from 10/90 to 90/10.

Perfluoropolyetherphosphate according to the present invention, which is represented by general formula (1), can be synthesized by a method according to JP Patent No. 3888902 and is marketed from Nikko Chemicals Co., Ltd. under the product name of FOMBLIN HC/P2-1000 (polyperfluoroethoxymethoxydifluoro ethyl PEG phosphate). The anionic polymer having a perfluoropolyether chain, which is represented by general formula (2), can be synthesized by a method according to JP Patent Publication (Kokai) No. 2003-129394 A and is marketed from Nikko Chemicals Co., Ltd. under the product name of FOMBLIN HC/PU-AN5E (polyurethane-27). The cationic polymer having a perfluoropolyether chain, which is represented by general formula (3), can be synthesized by a method according to JP Patent Publication (Kokai) No. 2000-302938 A and is marketed from Nikko Chemicals Co., Ltd. under the product name of FOMBLIN HC/PU-CAT5 (polyurethane-26).

There are generally two methods, a wet method and a dry method, as methods for treating the surface of a material powder using a surface treatment agent. A wet method involves dispersing a material powder in a solvent or a water/solvent solution, adding a surface treatment agent with stirring to the dispersion, filtering after uniform coating, and then drying so as to obtain a surface-treated powder. A dry method involves adding a material powder to a Henschel mixer, a ball mill, or the like, adding a surface treatment agent dissolved in a solvent, mixing well, drying, and then heating so as to obtain a treated powder.

Methods for surface treatment to be used in the present invention are not particularly limited, but a wet method is preferable for homogeneous surface treatment. Specifically, perfluoropolyetherphosphate represented by general formula (1) and the anionic polymer containing a perfluoropolyether chain, which is represented by general formula (2), are dissolved in water under alkaline conditions, and the cationic polymer containing a perfluoropolyether chain, which is represented by general formula (3), is dissolved in water under acidic conditions. Therefore, for treatment with perfluoropolyetherphosphate represented by general formula (1) and the anionic polymer containing a perfluoropolyether chain, which is represented by general formula (2), a material powder is dispersed in water, the surface treatment agents are added under alkaline conditions of pH 8.0 or more, preferably pH 9.0 or more, and further preferably pH 9.5 or more, the resultant is mixed well, and then the agents are caused to homogeneously adsorb to the surface of the material powder. Then insolubilization was performed under acidic conditions, so that the surface treatment agent is caused to strongly adsorb to the material powder. Subsequently, filtration and drying are performed, so that a surface-treated powder can be obtained.

Similarly, for treatment with the cationic polymer containing a perfluoropolyether chain, which is represented by general formula (3), a material powder is dispersed in water, the surface treatment agents are added under acidic conditions of pH 6.0 or less, preferably pH 5.0 or less, and further preferably at pH 4.5 or less, the resultant is mixed well, it is caused to homogenously adsorb to the surface of the material powder, insolubilization is performed under alkaline conditions, so that the surface treatment agents are caused to strongly adsorb to the material powder. Subsequently, filtration and then drying are performed, so that a surface-treated powder can be obtained.

The surface-treated powder of the present invention obtained as described above is excellent in water repellency and oil repellency, and has smooth texture and good adhesion when applied to skin. Water repellency and oil repellency can be measured by known methods. For example, a sample is added to a flat vessel, a flat surface is formed with a force of 100 kg/cm$^2$, aqueous droplets and squalane droplets are gently added dropwise to the surface, and then the resulting contact angles are measured. The thus measured water repellency of surface-treated powder of the present invention is 50 or more, preferably 90 or more, further preferably 100 or more, further more preferably 115 or more, even further more preferably 120 or more, and particularly preferably 125 or more. The thus measured oil repellency of the same is 20 or more, preferably 30 or more, further preferably 35 or more, further more preferably 40 or more, and particularly preferably 50 or more. Adhesiveness to skin can be determined by homogeneously rubbing a sample into the upper-inner arm, brushing away, visually observing the remainder adhering to the spot, and then comparing the state of the sample adhering thereto with that of an untreated powder. The term "smooth texture when applied to skin" refers to smoothness when a surface-treated powder is applied to skin. For example, smoothness can also be determined through comparison with an untreated powder.

Also, a material powder is treated in advance with a surface treatment aid, so that an even better surface-treated powder can be obtained in the present invention. Examples of a surface treatment aid include iron chloride, aluminium chloride, aluminium chloride hexahydrate, aluminium hydroxide, aluminium silicate, and aluminium phosphate. A preferable example thereof is aluminium chloride hexahydrate. The amounts of these surface treatment aids (to be used herein) are not limited. To obtain a good surface-treated powder without losing the effects of the present invention, the amount of a surface treatment aid preferably ranges from about 0.1 to 5 parts by mass with respect to 100 parts by mass of the surface-treated powder.

Furthermore, upon surface treatment of the material powder according to the present invention, surface treatment of a material powder can be performed using surface treatment agents other than the surface treatment agents represented by general formulae (1) to (3) simultaneously or successively, as long as the effects of the present invention are not compromised. Here, the term "(using or used) simultaneously" means that the surface treatment agents represented by general formulae (1) and (2) or (1) and (3) are mixed with a surface treatment agent(s) other than the surface treatment agents represented by general formulae (1) to (3) and then treatment is performed with the mixture. The term "(using or used) successively" means that after treatment with the surface treatment agents represented by (1) and (2) or (1) and (3), treatment is performed using a surface treatment agent(s) other than the surface treatment agents represented by general formulae (1) to (3), or after treatment with a surface treatment agent(s) other than the surface treatment agents represented by general formulae (1) to (3), and then treatment is performed with the surface treatment agents represented by (1) and (2) or (3). Examples of surface treatment agents (that can be used in the present invention) other than the surface treatment agents represented by general formulae (1) to (3) include, but are not limited to: fluorinated compounds other than the surface treatment agents according to the present invention, such as perfluoropolyether-modified amino silane, perfluorooctyltriethoxy $C_{9-15}$ fluoroalcohol phosphate, trifluoropropylcyclopentasiloxane, and PEG8 trifluoropropyl dimethicone copolymer; silicone compounds such as hydrogen silicone, amino silicone, reactive organopolysiloxane, and alkylsilane; lecithins such as organic titanate, polyolefin, lecithin and/or a salt thereof, and hydrogenated lecithin and/or a salt thereof; acylated amino acid and/or a salt thereof; acid ester oil; fatty acid and/or salts thereof; dextrin fatty acid ester; fructooligosaccharide fatty acid ester; collagen; higher alcohol; ester; wax; and metal soap.

The above perfluoropolyether-modified amino silane can be synthesized by a method according to JP Patent Publication (Kokai) No. 58-122979 A (1983). Perfluorooctyltriethoxy silane produced by Gelest, can be used herein. $C_{9-15}$ fluoroalcohol phosphate can be synthesized by a method according to JP Patent Publication (Kokai) No. 2004-277389 A. As trifluoropropylcyclopentasiloxane, KF-5002 (Shin-Etsu Chemical Co., Ltd.) or the like can be used herein. As PEG8 trifluoropropyl dimethicone, FPD-6131 (Shin-Etsu Chemical Co., Ltd.) or the like can be used, for example. As reactive organopolysiloxane, KF99 (methicone), KF9901 (hydrogen dimethicone), KF-9908 (triethoxysilylethyl polydimethylsiloxyethyl dimethicone), KF-9909 (triethoxylyl ethyl polydimethylsiloxyethyl hexyl dimethicone), KP-574 ((acrylates/tridecyl acrylate/triethoxysilylpropyl methacrylate/dimethicone methacrylate) copolymer), KF-7312 (mixture of trimethylsiloxysilicate and cyclopentasiloxane), KF-9001 (50% decamethylcyclopentasiloxane solution of trimethylsiloxysilicate (Shin-Etsu Chemical Co., Ltd.) can be used herein, for example. As alkylsilane, Z-6341 (octyltriethoxysilane (Dow Corning Corporation)), F-8261 (tridecafluorooctyltriethoxysilane (Degussa)), and the like can be used herein. As organic titanate, Plenact KR-TTS (isopropyltriisostearoyltitanate (Ajinomoto Co., Inc.)) and the like can be used herein. As polyolefin, known compounds as disclosed in JP Patent Publication (Kokai) No. 63-179972 A (1988), polyethylene oxide obtained via oxidation of polypropylene, maleated polyethylene, polypropylene oxide, and the like can be used. As hydrogenated lecithin and/or salts thereof, Lecinol S-10 (hydrogenated lecithin (Nikko Chemicals Co., Ltd.)), yolk lecithin PL-100P (hydrogenated yolk phospholipid (Kewpie Corporation)), and the like can be used herein. As acylated amino acid and/or a salt thereof, sarcosinate MN (sodium myristoylmethyl aminoacetate (Nikko Chemicals Co., Ltd.)), alaninate LN-30 (sodium lauroyl methylaminophosphate), sarcosinate CN-30 (sodium cocoyl sarcosinate), sarcosinate OH (oleoyl sarcosine), Amisoft HS-21 (N-stearoyl-L-glutamic acid disodium (Ajinomoto Co., Inc.)), SEPILIFT DPHP (dipalmitoylhydroxyproline (SEPPIC)), and the like can be used.

The amounts of surface treatment agents to be used herein other than the surface treatment agents represented by (1) to (3) are not limited and preferably used to a degree such that the properties of the surface treatment agents of the present invention are not deteriorated. Preferably, the amount of a surface treatment aid other than the surface treatment agents represented by (1) to (3) ranges from about 0.1 to 10 parts by mass with respect to 100 parts by mass of a surface-treated powder.

A material powder to be used in the present invention is not particularly limited, as long as it is a powder that is conventionally used as a powder for cosmetics. Examples thereof are the following material powders. Furthermore, one, two or more types of these material powders may be mixed and then used.

Examples of such a material powder include: inorganic pigments such as iron oxide, zinc oxide, titanium oxide, cerium oxide, magnesium oxide, zirconium oxide, barium sulfate, chromium oxide, ultramarine blue, iron oxide red, magnesium carbonate, calcium carbonate, mica, sericite, talc, silica, kaolin, chromium hydroxide, zinc oxide (flower of zinc), carbon black, alumina, aluminium silicate, magnesium silicate, boron nitride, silica-alumina powder, bentonite, and smectite; organic powders such as nylon powder, polyurethane powder, polymethyl methacrylate, styrene-divinylbenzene copolymer, polyethylene powder, silicone resin, Teflon (trademark) powder, silicone gum, silk powder, carnauba wax, rice wax, starch, and microcrystalline cellulose; organic dyes such as rhodamine B; zirconium such as red No. 201, black No. 401, yellow No. 4, and blue No. 1; organic colorants such as barium or aluminum lake; compound powders such as titanated mica and iron oxide-coated mica; and surface-treated powders. The shape of such a material powder may be any shape, as long as the shape and the particle size thereof are generally employed for cosmetics, such as spherical, plate-like, needle-like, and fibrous shapes. The amount of surface treatment agents to be used for coating a material powder, which can be used for cosmetics, differs depending on the types and the particle sizes of a material powders, oil absorption, water absorption, specific surface area, and the like. The amount of a surface treatment agent having a perfluoropolyether chain according to the present invention, which is to be used for treatment, ranges from 0.5 to 40 parts by mass, preferably ranges from 1 to 20 parts by mass, and further preferably ranges from 2 to 10 parts by mass with respect to 100 parts by mass of a material powder. When the amount thereof is less than 0.5 parts by mass, sufficient effects cannot be obtained. When the amount thereof is higher than the above range, the properties of the surface treatment agent of the present invention are lost. Also, when surface treatment is performed using surface treatment agents, a material powders may bind to each other to form aggregates. In such a case, a surface-treated powder is pulverized using an atomizer or the like after surface treatment.

Next, the cosmetics of the present invention will be described in detail below.

The cosmetics of the present invention comprise the above surface-treated powder of the present invention. Any formulation thereof may be employed herein. Examples of the cosmetics generally include all cosmetics comprising conventional powders for cosmetics. Examples of these cosmetics include facial cosmetics such as foundation, face powder, and blush, and make up cosmetics such as eye shadow, mascara, eyeliner, eyebrow pencil, lipstick, and nail enamel, sunscreen cosmetics, and skincare cosmetics such as emulsion and lotion. Also, the cosmetics of the present invention can also be preferably used for skin external preparation, ointment, and the like, in addition to the above cosmetics.

The amount of the surface-treated powder of the present invention, which is to be mixed with cosmetics varies depending on the forms of cosmetics and generally ranges from 0.01% by mass to 99.9% by mass. Mixing with other cosmetic ingredients such as fragrances, and a mixing amount of less than 0.1% by mass result in insufficient water repellency, oil repellency effects, and texture of the surface-treated powder according to the present invention. When these are taken into consideration, the mixing amount of the surface-treated powder preferably ranges from 0.1% by mass to 99% by mass. In addition, an appropriate mixing amount of the surface-treated powder differs depending on the types of cosmetics. For example, the mixing amount thereof preferably ranges from 20% by mass to 80% by mass in the case of solid powder cosmetics, the mixing amount thereof preferably ranges from 5% by mass to 50% by mass in the case of creams, the mixing amount thereof further preferably ranges from 2% by mass to 30% by mass in the case of milky lotions, and the mixing amount thereof further preferably ranges from 2% by mass to 20% by mass in the case of lotions.

As components other than the surface-treated powder of the present invention can be mixed with the cosmetics of the present invention, components can be appropriately selected from components that are generally mixed with cosmetics and then used, depending on the types of cosmetics. Examples of these components include, but are not limited to, liquid paraffin, hydrocarbon such as Vaseline, vegetable oil, waxes, synthetic ester oil, silicone-based oil-phase components, fluorinated oil phase components, higher alcohols, lower alcohols, fatty acids, thickeners, UV absorbers, powders, inorganic or organic pigments, color materials, various surfactants, polyhydric alcohol, sugar, polymers, actives, penetration enhancers for transdermal applications, solvents, antioxidants, fragrances, preservatives, and various additives.

The cosmetics of the present invention can be produced according to a general method. Cosmetics produced by mixing the powder for cosmetics of the present invention are excellent in waterproof and sebum resistance, prevent makeup from wearing off due to sweat, sebum, and the like, have a smooth texture when the cosmetics are applied to skin, are excellent in adhesiveness, and can provide proper moisturization during use.

The present invention will be further described specifically with reference to examples. However, the technical scope of the present invention is not limited by the following examples.

EXAMPLES

Example 1

1. Production Method
(Method 1 for Producing Treated Powder)
Sericite (muscovite powder) (100 g) was weighed and added to a beaker, 100 g of purified water was added thereto, and then the mixture was stirred well. An aqueous sodium hydroxide solution was added to the mixture to adjust to pH 10, 2 g of FOMBLIN HC/P2-1000 was added, and then the solution was mixed for 30 minutes. Furthermore, 2 g of FOMBLIN HC/PU-AN5E was added and then the resultant was mixed for 30 minutes. The pH was adjusted to 4.5 with hydrochloric acid, the resultant was mixed for 10 minutes, and then fluid was filtered out. The residue was dried with a dryer at 100° C. for 8 hours, and then pulverized. The resultant was designated as product 1 of the present invention.

(Method 2 for Producing Treated Powder)

Sericite (100 g) was weighed and added to a beaker, 100 g of purified water was added, and then the mixture was stirred well. An aqueous sodium hydroxide solution was added to the mixture to adjust to pH 10, 2 g of FOMBLIN HC/P2-1000 was added and then the resultant was mixed for 30 minutes. The pH was adjusted to 4.5 with hydrochloric acid, 2 g of FOMBLIN HC/PU-CAT5 was added, and the mixture was stirred for 30 minutes, and then fluid was filtered out. The residue was dried with a dryer at 100° C. for 8 hours, and then pulverized. The resultant was designated as product 2 of the present invention.

(Method 3 for Producing Treated Powder)

Sericite (100 g) was weighed and added to a beaker, 100 g of purified water was added, and then the mixture was stirred well. An aqueous sodium hydroxide solution was added to the mixture to adjust to pH 10, 2 g of FOMBLIN HC/P2-1000 was added and then the resultant was mixed for 30 minutes. FOMBLIN HC/PU-AN5E (1 g) was added and then the resultant was mixed for 30 minutes. Hydrochloric acid was added to adjust to pH 4.5, 1 g of FOMBLIN HC/PU-CAT5 was added, and the mixture was stirred for 30 minutes, and then fluid was filtered out. The residue was dried with a dryer at 100° C. for 8 hours, and then pulverized. The resultant was designated as product 3 of the present invention.

(Method 4 for Producing Treated Powder)

Sericite (100 g) was weighed and added to a beaker, 100 g of purified water was added, and then the mixture was stirred well. An aqueous sodium hydroxide solution was added to the mixture to adjust to pH 10, 2 g of FOMBLIN HC/PU-AN5E was added, 2 g of FOMBLIN HC/P2-1000 was further added, and then the resultant was mixed for 30 minutes. Hydrochloric acid was added to adjust to pH 4.5. After mixing, fluid was filtered out. The residue was dried with a dryer at 100° C. for 8 hours, and then pulverized. The resultant was designated as product 4 of the present invention.

(Method 5 for Producing Treated Powder)

Sericite (100 g) was weighed and added to a beaker, 100 g of purified water was added, and then the mixture was stirred well. Aluminium chloride hexahydrate (1 g) was added and then sodium hydroxide was added to the mixture to adjust to pH 10 while stirring and mixing. FOMBLIN HC/P2-1000 (2 g) was added and then 2 g of FOMBLIN HC/PU-AN5E was further added, and then the resultant was mixed for 30 minutes. Hydrochloric acid was added to adjust to pH 4.5. After mixing, fluid was filtered out. The residue was dried with a dryer at 100° C. for 8 hours, and then pulverized. The resultant was designated as product 5 of the present invention.

(Method 6 for Producing Treated Powder)

Sericite (100 g) was weighed and added to a beaker, 100 g of purified water was added, and then the mixture was stirred well. Aluminium chloride hexahydrate (1 g) was added and then an aqueous sodium hydroxide solution was added to the mixture to adjust to pH 10 while stirring and mixing. FOMBLIN HC/P2-1000 (2 g) was added and then the resultant was mixed for 30 minutes. Hydrochloric acid was added to adjust to pH 4.5 and then 2 g of FOMBLIN HC/PU-CAT5 was further added. After 30 minutes of stirring, fluid was filtered out. The residue was dried with a dryer at 100° C. for 8 hours, and then pulverized. The resultant was designated as product 6 of the present invention.

(Method 7 for Producing Treated Powder)

Sericite (100 g) was weighed and added to a beaker, 100 g of purified water was added, and then the mixture was stirred well. Aluminium chloride hexahydrate (1 g) was added and then an aqueous sodium hydroxide solution was added to the mixture to adjust to pH 10 while stirring and mixing. FOMBLIN HC/P2-1000 (2 g) was added, 1 g of FOMBLIN HC/PU-AN5E was further added, and then the resultant was mixed for 30 minutes. Hydrochloric acid was added to adjust to pH 4.5 and then 1 g of FOMBLIN HC/PU-CAT5 was further added. After 30 minutes of stirring, fluid was filtered out. The residue was dried with a dryer at 100° C. for 8 hours, and then pulverized. The resultant was designated as product 7 of the present invention.

(Method 8 for Producing Treated Powder)

Sericite (100 g) was weighed and added to a beaker, 100 g of purified water was added, and then the mixture was stirred well. Sodium hydroxide was added to adjust to pH 10, FOMBLIN HC/P2-1000 (4 g) was added, and then the resultant was mixed for 30 minutes. Hydrochloric acid was added to adjust to pH 4.5. After mixing, fluid was filtered out. The residue was dried with a dryer at 100° C. for 8 hours, and then pulverized. The resultant was designated as comparative product 1.

(Method 9 for Producing Treated Powder)

Sericite (100 g) was weighed and added to a beaker, 100 g of purified water was added, and then the mixture was stirred well. Sodium hydroxide was added to adjust to pH 10, FOMBLIN HC/PU-AN5E (4 g) was added, and then the resultant was mixed for 30 minutes. Hydrochloric acid was added to adjust to pH 4.5. After mixing, fluid was filtered out. The residue was dried with a dryer at 100° C. for 8 hours, and then pulverized. The resultant was designated as comparative product 2.

(Method 10 for Producing Treated Powder)

Sericite (100 g) was weighed and added to a beaker, 100 g of purified water was added, and then the mixture was stirred well. Hydrochloric acid was added to adjust to pH 4.5 and then FOMBLIN HC/PU-CAT5 (4 g) was added. After 30 minutes of stirring, fluid was filtered out. The residue was dried with a dryer at 100° C. for 8 hours, and then pulverized. The resultant was designated as comparative product 3.

2. Evaluation Method (Water repellency and oil repellency) Samples were placed in flat vessels to form flat surfaces with a force of 100 kg/cm$^2$, aqueous droplets and squalane droplets were gently added dropwise onto the surfaces, and then the resulting contact angles were measured.

(Adhesiveness) Each sample was rubbed homogeneously into the upper-inner arm and then brushed away. The resulting spot to which the remaining sample adhered was visually observed and then evaluated using the following 5-point scores. The results were averaged.

5: Better adhesiveness than untreated powder
4: Relatively better adhesiveness than untreated powder
3: Similar in terms of adhesiveness to untreated powder
2: Relatively more easily disintegrated than untreated powder
1: Significantly more easily disintegrated than untreated powder (Texture) Five monitors participated in the test and evaluated smoothness upon application of samples using the following 5-point scores. The results were averaged.
5: Significantly better than untreated powder
4: Better than untreated powder
3: Similar to untreated powder
2: Relatively inferior to untreated powder
1: Significantly inferior to untreated powder 3. Evaluation Results Table 1 shows the evaluation results. Good powders were obtained regardless of variations in the combined use of FOMBLIN HC/P2-1000 and FOMBLIN HC/PU-AN5E or FOMBLIN HC/P2-1000 and FOMBLIN HC/PU-CAT5, variations in the order of treatment steps, and variations in methods for treatment. Also, with the method that involves adding aluminium chloride hexahydrate as a surface treatment aid, even better powder was obtained. Moreover, product 1 and product 2 of the present invention, for which surface treatment had been performed using surface treatment agents in combination, exhibited better water repellency, better oil repellency, and better texture than comparative products 1, 2, and 3, for which simple surface treatment had been performed.

Example 2

1. Production Method

Treated powders were produced according to "Method 1 for producing treated powder" or "Method 2 for producing treated powder" in Example 1.

2. Evaluation Method (Water repellency and oil repellency) Samples were placed in flat vessels to form flat surfaces with a force of 100 kg/cm$^2$, aqueous droplets and squalane droplets are gently added dropwise onto the surfaces, and then the resulting contact angles were measured.

(Texture) Five monitors participated in the test and evaluated smoothness upon application of samples with the following 5-point scores. The results were averaged.
5: Significantly better than untreated powder
4: Better than untreated powder
3: Similar to untreated powder
2: Relatively inferior to untreated powder
1: Significantly inferior to untreated powder 3. Evaluation Results The effects of the surface treatment agents of the present invention appeared with treated amount of 0.5-40 parts by mass with respect to 100 parts by mass of each surface-treated powder. With treated amount of 2-20 parts by mass, powders excellent in water repellency, oil repellency, and texture were obtained.

TABLE 1

| | Surface treatment agent | Treated Amount (parts by mass) | Powder type | Water repellency | Oil repellency | Adhesiveness | Texture |
|---|---|---|---|---|---|---|---|
| Product 1 of the present invention | HC/P2-1000<br>HC/PU-AN5E | 2<br>2 | Sericite | 126 | 58 | 3.8 | 4.2 |
| Product 2 of the present invention | HC/P2-1000<br>HC/PU-CAT5 | 2<br>2 | Sericite | 128 | 60 | 4.4 | 4.2 |
| Product 3 of the present invention | HC/P2-1000<br>HC/PU-AN5E<br>HC/PU-CAT5 | 2<br>1<br>1 | Sericite | 127 | 57 | 4.2 | 4.0 |
| Product 4 of the present invention | HC/PU-AN5E<br>HC/P2-1000 | 2<br>2 | Sericite | 126 | 55 | 3.8 | 3.8 |
| Product 5 of the present invention | AlCl$_3$•6H$_2$O<br>HC/P2-1000<br>HC/PU-AN5E | 1<br>2<br>2 | Sericite | 134 | 62 | 4.6 | 4.4 |
| Product 6 of the present invention | AlCl$_3$•6H$_2$O<br>HC/P2-1000<br>HC/PU-CAT5 | 1<br>2<br>2 | Sericite | 131 | 64 | 4.8 | 4.8 |
| Product 7 of the present invention | AlCl$_3$•6H$_2$O<br>HC/P2-1000<br>HC/PU-AN5E<br>HC/PU-CAT5 | 1<br>2<br>1<br>1 | Sericite | 132 | 61 | 4.6 | 4.8 |
| Comparative product 1 | HC/P2-1000 | 4 | Sericite | 113 | 29 | 2.4 | 2.8 |
| Comparative product 2 | HC/PU-AN5E | 4 | Sericite | 95 | 10 | 2.8 | 2.4 |
| Comparative product 3 | HC/PU-CAT5 | 4 | Sericite | 100 | 22 | 3.2 | 2.8 |

TABLE 2

| | Surface treatment agent | Treated Amount (parts by mass) | Powder type | Water repellency | Oil repellency | Texture |
|---|---|---|---|---|---|---|
| Product 1-1 of the present invention | HC/P2-1000 HC/PU-AN5E | 0.25 0.25 | sericite | 55 | 20 | 2.6 |
| Product 1-2 of the present invention | HC/P2-1000 HC/PU-AN5E | 1 1 | sericite | 97 | 28 | 3.8 |
| Product 1-3 of the present invention | HC/P2-1000 HC/PU-AN5E | 2 2 | sericite | 126 | 58 | 4.2 |
| Product 1-4 of the present invention | HC/P2-1000 HC/PU-AN5E | 5 5 | sericite | 122 | 57 | 3.8 |
| Product 1-5 of the present invention | HC/P2-1000 HC/PU-AN5E | 10 10 | sericite | 110 | 39 | 3.0 |
| Product 1-6 of the present invention | HC/P2-1000 HC/PU-AN5E | 20 20 | sericite | 99 | 29 | 2.8 |
| Product 2-1 of the present invention | HC/P2-1000 HC/PU-CAT5 | 0.25 0.25 | sericite | 60 | 20 | 3.0 |
| Product 2-2 of the present invention | HC/P2-1000 HC/PU-CAT5 | 1 1 | sericite | 100 | 30 | 3.8 |
| Product 2-3 of the present invention | HC/P2-1000 HC/PU-CAT5 | 2 2 | sericite | 128 | 60 | 4.2 |
| Product 2-4 of the present invention | HC/P2-1000 HC/PU-CAT5 | 5 5 | sericite | 122 | 57 | 4.4 |
| Product 2-5 of the present invention | HC/P2-1000 HC/PU-CAT5 | 10 10 | sericite | 110 | 40 | 3.8 |
| Product 2-6 of the present invention | HC/P2-1000 HC/PU-CAT5 | 20 20 | sericite | 101 | 31 | 3.2 |

Example 3

The treated amount of each surface treatment agent with respect to 100 parts by mass of each surface-treated powder was fixed to 4.0 parts by mass (with this treated amount, the best water water repellency and the best oil repellency were obtained in Example 2), the mixing ratio of FOMBLIN HC/P2-1000 to FOMBLIN HC/PU-AN5E, and the mixing ratio of FOMBLIN HC/P2-1000 to FOMBLIN HC/PU-CAT5 were varied, and then surface-treated powders were evaluated.
1. Production Method
Treated powders were produced according to "Method 1 for producing treated powder" or "Method 2 for producing treated powder" in Example 1.
2. Evaluation Method
(Water repellency and oil repellency) Samples were placed in flat vessels to form flat surfaces with a force of 100 kg/cm², aqueous droplets and squalane droplets are gently added dropwise onto the surfaces, and then the resulting contact angles were measured.

(Texture) Five monitors participated in the test and evaluated smoothness upon application of samples with the following 5-point scores. The results were averaged.
5: Significantly better than untreated powder
4: Better than untreated powder
3: Similar to untreated powder
2: Relatively inferior to untreated powder
1: Significantly inferior to untreated powder
3. Evaluation Results
Table 3 shows the results. As the amount of FOMBLIN HC/PU-AN5E or FOMBLIN HC/PU-CAT5 increased with respect to the amount of FOMBLIN HC/P2-1000, powders excellent in texture, water repellency, and oil repellency were obtained. When the mixing amount of FOMBLIN HC/PU-AN5E was 0.1 parts by mass or less, poor texture were obtained. When the mixing amount of FOMBLIN HC/P2-1000 was 0.1 parts by mass or less, oil repellency was not obtained and smooth texture were not sufficiently obtained.

TABLE 3

| | Surface treatment agent | Treated Amountt (parts by mass) | Powder type | Water repellency | Oil repellency | Texture |
|---|---|---|---|---|---|---|
| Product 1-7 of the present invention | HC/P2-1000 HC/PU-AN5E | 3 1 | sericite | 125 | 57 | 3.2 |

TABLE 3-continued

| | Surface treatment agent | Treated Amount (parts by mass) | Powder type | Water repellency | Oil repellency | Texture |
|---|---|---|---|---|---|---|
| Product 1-8 of the present invention | HC/P2-1000 HC/PU-AN5E | 2 2 | sericite | 126 | 58 | 4.2 |
| Product 1-9 of the present invention | HC/P2-1000 HC/PU-AN5E | 1 3 | sericite | 120 | 57 | 3.8 |
| Product 2-7 of the present invention | HC/P2-1000 HC/PU-CAT5 | 3.9 0.1 | sericite | 122 | 51 | 2.0 |
| Product 2-8 of the present invention | HC/P2-1000 HC/PU-CAT5 | 3.5 0.5 | sericite | 122 | 57 | 2.8 |
| Product 2-9 of the present invention | HC/P2-1000 HC/PU-CAT5 | 3 1 | sericite | 128 | 59 | 4.2 |
| Product 2-10 of the present invention | HC/P2-1000 HC/PU-CAT5 | 2 2 | sericite | 128 | 60 | 4.2 |
| Product 2-11 of the present invention | HC/P2-1000 HC/PU-CAT5 | 1 3 | sericite | 132 | 61 | 4.6 |
| Product 2-12 of the present invention | HC/P2-1000 HC/PU-CAT5 | 0.5 3.5 | sericite | 130 | 40 | 3.6 |
| Product 2-13 of the present invention | HC/P2-1000 HC/PU-CAT5 | 0.1 3.9 | sericite | 130 | 30 | 2.2 |

Example 4

The compound having a perfluoropolyether chain and perfluoropolyetherphosphate of the present invention were added and surface treatment agents other than those represented by general formulae (1) to (3) were separately added, so that such combined uses thereof were evaluated.

1. Production Method

Treated powders were produced according to "Method 2 for producing treated powder" in Example 1.

2. Evaluation Method (Water repellency and oil repellency) Samples were placed in flat vessels to form flat surfaces with a force of 100 kg/cm$^2$, aqueous droplets and squalane droplets are gently added dropwise onto the surfaces, and then the resulting contact angles were measured.

(Texture) Five monitors participated in the test and evaluated smoothness upon application of samples with the following 5-point scores. The results were averaged.

5: Significantly better than untreated powder

4: Better than untreated powder

3: Similar to untreated powder

2: Relatively inferior to untreated powder

1: Significantly inferior to untreated powder

3. Evaluation Results

Water repellency, oil repellency, and texture were obtained with the use of many combinations to the same degrees as in the case of using silane alone. In this experiment, synergistically improved functions were observed by the combined use with perfluoropolyetherphosphate.

TABLE 4

| | Surface treatment agent | Treated Amount (parts by mass) | Powder type | Water repellency | Oil repellency | Texture |
|---|---|---|---|---|---|---|
| Product 8 of the present invention | HC/P2-1000 HC/PU-CAT5 Hydrogen silicone | 1.0 3.0 0.5 | sericite | 130 | 59 | 4.2 |
| Product 9 of the present invention | HC/P2-1000 HC/PU-CAT5 Perfluoro polyether-modified aminosilane | 1.0 3.0 0.5 | sericite | 130 | 59 | 4.4 |
| Product 10 of the present invention | HC/P2-1000 HC/PU-CAT5 Perfluoro octylalkyl phosphate DEA | 1.0 3.0 0.5 | sericite | 130 | 59 | 4.2 |

TABLE 4-continued

| | Surface treatment agent | Treated Amount (parts by mass) | Powder type | Water repellency | Oil repellency | Texture |
|---|---|---|---|---|---|---|
| Product 11 of the present invention | HC/P2-1000<br>HC/PU-CAT5<br>Perfluoro octyl triethoxy silane | 1.0<br>3.0<br>0.5 | sericite | 128 | 58 | 4.2 |
| Product 12 of the present invention | HC/P2-1000<br>HC/PU-CAT5<br>Trifluoro propylcyclo penta-siloxane | 1.0<br>3.0<br>0.5 | sericite | 129 | 59 | 3.6 |
| Product 13 of the present invention | HC/P2-1000<br>HC/PU-CAT5<br>Perfluoro alkyl(C4-14) ethoxy Dimethicone | 1.0<br>3.0<br>0.5 | sericite | 128 | 58 | 3.8 |
| Product 14 of the present invention | HC/P2-1000<br>HC/PU-CAT5<br>Isopropyl isostearoyl titanate | 1.0<br>3.0<br>0.5 | sericite | 128 | 58 | 3.6 |

Example 5

Makeup Base

1. Production Method (Method 11 for Producing Treated Powder)

A cross polymer (diphenyl dimethicone/vinylphenyl dimethicone/silsesquioxane) (100 g) was weighed and added to a beaker, 100 g of purified water was added, and then the mixture was stirred well. Sodium hydroxide was added to the mixture to adjust to pH 10, 1 g of FOMBLIN HC/P2-1000 was added and then the resultant was mixed for 30 minutes. The pH was adjusted to 4.5 with hydrochloric acid and then 3 g of FOMBLIN HC/PU-CAT5 was added. After 30 minutes of stirring, fluid was filtered out. The residue was dried with a dryer at 100° C. for 8 hours, and then pulverized. The resultant was designated as product 15 of the present invention.

(Method 12 for Producing Treated Powder)

Titanium oxide (100 g) was weighed and added to a beaker, 100 g of purified water was added, and then the mixture was stirred well. Sodium hydroxide was added to the mixture to adjust to pH 10, 1 g of FOMBLIN HC/P2-1000 was added, and then the resultant was mixed for 30 minutes. The pH was adjusted to 4.5 with hydrochloric acid and then 3 g of FOMBLIN HC/PU-CAT5 was added. After 30 minutes of stirring, fluid was filtered out. The residue was dried with a dryer at 100° C. for 8 hours, and then pulverized. The resultant was designated as product 16 of the present invention.

(Method 13 for Producing Treated Powder)

Iron oxide (100 g) was weighed and added to a beaker, 100 g of purified water was added, and then the mixture was stirred well. Sodium hydroxide was added to the mixture to adjust to pH 10, 1 g of FOMBLIN HC/P2-1000 was added and then the resultant was mixed for 30 minutes. The pH was adjusted to 4.5 with hydrochloric acid and then 3 g of FOMBLIN HC/PU-CAT5 was added. After 30 minutes of stirring, fluid was filtered out. The residue was dried with a dryer at 100° C. for 8 hours, and then pulverized. The resultant was designated as product 17 of the present invention.

2. Formulation

| | | |
|---|---|---|
| A | Water | Remainder (% by mass) |
| | Glycerin | 5 |
| | Stearoxy PG hydroxyl PG hydroxyethyl sulfonate Na | 2 |
| B | Perfluoroalkyl(C4-14)ethoxy dimethicone | 13 |
| | Cyclomethicone | 10 |
| | Dimethicone | 6 |
| | Octyl methoxyeinnamate | 4 |
| | Ethanol | 3 |
| | Isostearylglycerin | 3 |
| | 1,3-butyleneglycol | 2 |
| | Carbomer (4% aqueous solution) | 2 |
| | Nylon 12 | 2 |
| | Surface-treated (diphenyl dimethicone/vinylphenyl dimethicone/silsesquioxane) cross polymer (product 15 of the present invention) | 2 |
| | Surface-treated titanium oxide (product 16 of the present invention) | 2 |
| | Surface-treated iron oxide (product 17 of the present invention) | 2 |

(Preparation method) While stirring phase A with a homomixer at room temperature, phase B was added for emulsification.

(Result) A makeup base with SPF25/PA++ and good water repellency, oil repellency, and texture was obtained.

Example 6

Powdery Foundation

1. Production Method (Method 14 for Producing Treated Powder)

Mica (100 g) was weighed and added to a beaker, 100 g of purified water was added, and then mixture was stirred well. Sodium hydroxide was added to the mixture to adjust to pH 10, 1 g of FOMBLIN HC/P2-1000 was added, and then the resultant was mixed for 30 minutes. The pH was adjusted to 4.5 with hydrochloric acid and then 3 g of FOMBLIN HC/PU-CAT5 was added. After 30 minutes of stirring, fluid was filtered out. The residue was dried with a dryer at 100° C. for 8 hours, and then pulverized. The resultant was designated as product 18 of the present invention.

(Method 15 for Producing Treated Powder)

Talc (100 g) was weighed and added to a beaker, 100 g of purified water was added, and then the mixture was stirred well. Sodium hydroxide was added to adjust to pH 10, 1 g of FOMBLIN HC/P2-1000 was added, and then the resultant was mixed for 30 minutes. The pH was adjusted to 4.5 with hydrochloric acid and then 3 g of FOMBLIN HC/PU-CAT5 was added. After 30 minutes of stirring, fluid was filtered out. The residue was dried with a dryer at 100° C. for 8 hours, and then pulverized. The resultant was designated as product 19 of the present invention.

(Method 16 for Producing Treated Powder)

Synthetic fluorphlogopite (100 g) was weighed and added to a beaker, 100 g of purified water was added, and then the mixture was stirred well. Sodium hydroxide was added to adjust to pH 10, 1 g of FOMBLIN HC/P2-1000 was added, and then the resultant was mixed for 30 minutes. The pH was adjusted to 4.5 with hydrochloric acid and then 3 g of FOMBLIN HC/PU-CAT5 was added. After 30 minutes of stirring, fluid was filtered out. The residue was dried with a dryer at 100° C. for 8 hours, and then pulverized. The resultant was designated as product 20 of the present invention.

2. Formulation

| A | Surface-treated mica (product 18 of the present invention) | Remainder (% by mass) |
|---|---|---|
| | Surface-treated talc (product 19 of the present invention) | 15 |
| | Surface-treated synthetic phlogopite (product 20 of the present invention) | 10 |
| | Nylon 12 | 10 |
| B | Dimethicone | 7 |
| | Isocetyl myristate | 5 |
| | Octyl methoxycinnamate | 5 |
| | (Diphenyl dimethicone/vinylphenyl dimethicone/silsesquioxane) cross polymer | 3 |
| | Tri(capryl/capric acid)glyceryl | 3 |
| | Hydrogenated polyisobutene | 3 |

(Preparation method) Phase B was mixed well. Phase A was added and then the mixture was further mixed therewith until it became uniform. A vessel filled with the mixture was designated as a product.

(Results) A foundation with SPF25/PA++, good water repellency, good oil repellency, and good texture was obtained.

Example 7

Liquid Foundation

1. Production Method (Method 17 for Producing Treated Powder)

Zinc oxide (100 g) was weighed and added to a beaker, 100 g of purified water was added, and then the resultant was stirred well. Sodium hydroxide was added to the mixture to adjust to pH 10, 1 g of FOMBLIN HC/P2-1000 was added, and then the resultant was mixed for 30 minutes. The pH was adjusted to 4.5 with hydrochloric acid and then 3 g of FOMBLIN HC/PU-CAT5 was added. After 30 minutes of stirring, fluid was filtered out. The residue was dried with a dryer at 100° C. for 8 hours, and then pulverized. The resultant was designated as product 21 of the present invention.

2. Formulation

| A | Purified water | Remainder (% by mass) |
|---|---|---|
| | Butyleneglycol | 5.0 |
| | Glycerin | 2.0 |
| | Pemulen | 0.1 |
| | Phenoxyethanol | 3.0 |
| B | Cyclopentasiloxane | 20.0 |
| | Surface-treated titanium oxide (product 16 of the present invention) | 5.0 |
| | Surface-treated zinc oxide (product 21 of the present invention) | 6.0 |
| | PEG-9 polydimethylsiloxyethyl dimethicone | 2.0 |
| | (Alkyl acrylateidimethicone) copolymer | 2.0 |
| | (Dimethicone/vinyl dimethicone) cross polymer | 2.0 |
| | Phytosterol isostearate | 1.0 |
| | Color material | 0.9 |

(Preparation method) Phase B was mixed well with a dispermixer. The resultant was added to phase A prepared as a uniform solution while stirring using a homomixer for emulsification.

(Results) An emulsified foundation excellent in water repellency and oil repellency was obtained. The foundation exhibited UV protective capacity as high as SPF20, PA++.

Example 8

W/O UV-protective Cosmetics

1. Production Method (Method 18 for Producing Treated Powder)

Zinc oxide (100 g) was weighed and added to a beaker, 100 g of purified water was added, and then the mixture was stirred well. Sodium hydroxide was added to the mixture to adjust to pH 10, 2 g of FOMBLIN HC/P2-1000 was added, and then the resultant was mixed for 30 minutes. FOMBLIN HC/PU-AN5E (1 g) was further added and then the resultant was mixed for 30 minutes. Hydrochloric acid was added to adjust to pH 4.5, and then 1 g of FOMBLIN HC/PU-CAT5 was added. After 30 minutes of stirring, fluid was filtered out. The residue was dried with a dryer at 100° C. for 8 hours, and then pulverized. The resultant was designated as product 22 of the present invention.

(Method 19 for Producing Treated Powder)

Titanium oxide (100 g) was weighed and added to a beaker, 100 g of purified water was added, and then the mixture was stirred well. Sodium hydroxide was added to the mixture to adjust to pH 10, 2 g of FOMBLIN HC/P2-1000 was added, and then the resultant was mixed for 30 minutes. FOMBLIN HC/PU-AN5E (1 g) was further added and then the resultant was mixed for 30 minutes. Hydrochloric acid was added to adjust to pH 4.5, and then 1 g of FOMBLIN HC/PU-CAT5 was added. After 30 minutes of stirring, fluid was filtered out. The residue was dried with a dryer at 100° C. for 8 hours, and then pulverized. The resultant was designated as product 23 of the present invention.

(Method 20 for Producing Treated Powder)

Talc (100 g) was weighed and added to a beaker, 100 g of purified water was added, and then the mixture was stirred well. Sodium hydroxide was added to the mixture to adjust to pH 10, 2 g of FOMBLIN HC/P2-1000 was added, and then the resultant was mixed for 30 minutes. FOMBLIN HC/PU-AN5E (1 g) was further added and then the resultant was mixed for 30 minutes. Hydrochloric acid was added to adjust to pH 4.5, and then 1 g of FOMBLIN HC/PU-CAT5 was added. After 30 minutes of stirring, fluid was filtered out fluid. The residue was dried with a dryer at 100° C. for 8 hours, and then pulverized. The resultant was designated as product 24 of the present invention.

(Method 21 for Producing Treated Powder)

Synthetic phlogopite (100 g) was weighed and added to a beaker, 100 g of purified water was added, and then the mixture was stirred well. Sodium hydroxide was added to the mixture to adjust to pH 10, 2 g of FOMBLIN HC/P2-1000 was added, and then the resultant was mixed for 30 minutes. FOMBLIN HC/PU-AN5E (1 g) was further added and then the resultant was mixed for 30 minutes. Hydrochloric acid was added to adjust to pH 4.5, and then 1 g of FOMBLIN HC/PU-CAT5 was added. After 30 minutes of stirring, fluid was filtered out. The residue was dried with a dryer at 100° C. for 8 hours, and then pulverized. The resultant was designated as product 25 of the present invention.

2. Formulation

| A | Dimethicone | 10.0 |
|---|---|---|
| | Diphenyl siloxy phenyl trimethicone | 5.0 |
| | (Dimethicone/methicone) · copolymer | 6.0 |
| | Ceresin | 5.0 |
| | Trimethylol propane trioctanoate | 5.0 |
| | Sorbitan sesquiisostearate | 4.0 |
| | Carnauba wax | 1.0 |
| | Surface-treated zinc oxide (product 22 of the present invention) | 10.0 |
| | Surface-treated titanium oxide (product 23 of the present invention) | 2.0 |
| | Surface-treated talc (product 24 of the present invention) | 2.0 |
| | Surface-treated synthetic phlogopite (product 25 of the present invention) | 2.0 |
| | Cyclomethicone | 3.0 |
| | Octyl methoxycinnarnate | 3.0 |
| | Mineral oil | 1.0 |
| | Vaseline | 1.0 |
| B | Dipropylene glycol | 2.0 |
| | Sodium Hyaluronate | 0.2 |
| | Water | Remainder (% by mass) |

(Preparation method) Phase A was heated to 70° C. Ingredients other than the powder of the present invention were dissolved uniformly. Phase B was gradually added to phase A while slowly stirring the mixture with a homomixer or a disper-mixer, and then the mixture was strongly stirred for emulsification.

(Results) W/O-type UV-protective cosmetics (SPF30, PA+++) that were excellent in water repellency and oil repellency and had good texture during use were obtained. Furthermore, the treated powder of the present invention had high dispersibility and exhibited high UV-protective capacity.

Example 9

UV-protective Foundation

1. Production Method (Method 22 for Producing Treated Powder)

Talc (100 g) was weighed and added to a beaker, 100 g of purified water was added, and then the mixture was stirred well. Sodium hydroxide was added to the mixture to adjust to pH 10, 2 g of FOMBLIN HC/P2-1000 and 1 g of isopropyltriisostearoyltitanate were added, and then the resultant was mixed for 30 minutes. FOMBLIN HC/PU-AN5E (1 g) was further added and then the resultant was mixed for 30 minutes. Hydrochloric acid was added to adjust to pH 4.5, and then 1 g of FOMBLIN HC/PU-CAT5 was added. After 30 minutes of stirring, fluid was filtered out. The residue was dried with a dryer at 100° C. for 8 hours, and then pulverized. The resultant was designated as product 26 of the present invention.

(Method 23 for Producing Treated Powder)

Synthetic phlogopite (100 g) was weighed and added to a beaker, 100 g of purified water was added, and then the mixture was stirred well. Sodium hydroxide was added to the mixture to adjust to pH 10, 2 g of FOMBLIN HC/P2-1000 and 1 g of isopropyltriisostearoyltitanate were added, and then the resultant was mixed for 30 minutes. FOMBLIN HC/PU-AN5E (1 g) was further added and then the resultant was mixed for 30 minutes. Hydrochloric acid was added to adjust to pH 4.5, and then 1 g of FOMBLIN HC/PU-CAT5 was added. After 30 minutes of stirring, fluid was filtered out. The residue was dried with a dryer at 100° C. for 8 hours, and then pulverized. The resultant was designated as product 27 of the present invention.

(Method 24 for Producing Treated Powder)

Zinc oxide (100 g) was weighed and added to a beaker, 100 g of purified water was added, and then the mixture was stirred well. Sodium hydroxide was added to the mixture to adjust to pH 10, 2 g of FOMBLIN HC/P2-1000 and 1 g of isopropyltriisostearoyltitanate were added, and then the resultant was mixed for 30 minutes. FOMBLIN HC/PU-AN5E (1 g) was further added and then the resultant was mixed for 30 minutes. Hydrochloric acid was added to adjust to pH 4.5, and then 1 g of FOMBLIN HC/PU-CAT5 was added. After 30 minutes of stirring, fluid was filtered out. The residue was dried with a dryer at 100° C. for 8 hours, and then pulverized. The resultant was designated as product 28 of the present invention.

2. Formulation

| Surface-treated talc (product 26 of the present invention) | Remainder (% by mass) |
|---|---|
| Surface-treated synthetic phlogopite (product 27 of the present invention) | 10 |
| Surface-treated zinc oxide (product 28 of the present invention) | 5 |

-continued

| | | |
|---|---|---|
| | Octyl methoxycinnamate | 6 |
| | Mineral oil | 5 |
| | Fine-particle silica | 3 |
| | Phytosteryl isostearate | 3 |
| | Dimethicone | 3 |
| | Nylon powder | 3 |
| | Triethyl hexanoin | 3 |
| | Water | 3 |
| | Polyglyceryl-2 triisostearate | |
| | Color material | 1 |

(Preparation method) The above ingredients were mixed until it became uniform with a Henschel mixer. A vessel filled with the resultant was designated as a product.

(Results) A foundation (SPF20, PA++) that was excellent in application, smoothness, and adhesiveness to skin, and dispersibility to oil, and had no color phase irregularity was obtained.

Example 10

Protect Emulsion

1. Production Method (Method 25 for Producing Treated Powder)

Titanium oxide (100 g) was weighed and added to a beaker, 100 g of purified water was added, and then the mixture was stirred well. Sodium hydroxide was added to the mixture to adjust to pH 10, 2 g of FOMBLIN HC/P2-1000 was added, and then the resultant was mixed for 30 minutes. FOMBLIN HC/PU-AN5E (1 g) was further added and then the resultant was mixed for 30 minutes. Hydrochloric acid was added to adjust to pH 4.5, and then 1 g of FOMBLIN HC/PU-CAT5 was added. After 30 minutes of stirring, fluid was filtered out. Hydrogen silicone (Shin-Etsu Chemical Co., Ltd. KF99) (1 g) was added. The resultant was pulverized with a Henschel mixer and then heated at 130° C. The resultant was designated as product 29 of the present invention.

(Method 26 for Producing Treated Powder)

Iron oxide (100 g) was weighed and added to a beaker, 100 g of purified water was added, and then the mixture was stirred well. Sodium hydroxide was added to the mixture to adjust to pH 10, 2 g of FOMBLIN HC/P2-1000 was added, and then the resultant was mixed for 30 minutes. FOMBLIN HC/PU-AN5E (1 g) was further added and then the resultant was mixed for 30 minutes. Hydrochloric acid was added to adjust to pH 4.5 and then 1 g of FOMBLIN HC/PU-CAT5 was added. After 30 minutes of stirring, fluid was filtered out. Hydrogen silicone (Shin-Etsu Chemical Co., Ltd. KF99) (1 g) was added. The resultant was pulverized with a Henschel mixer and then heated at 130° C. The resultant was designated as product 30 of the present invention.

2. Formulation

| | | |
|---|---|---|
| A | Water | Remainder (% by mass) |
| | Ethanol | 15.0 |
| | Glycerin | 6.0 |
| | Butylene glycol | 3.0 |
| | Stearoxy PG hydroxyethyl cellulose sulfonate Na | 1.0 |
| | Silicone copolyol | 1.0 |
| B | Octyl methoxycinnainate | 5.0 |
| | Perfluoroalkyl(C4-14)ethoxy dimethicone | 5.0 |
| | Cyclomethicone | 5.0 |
| | Dimethicone | 5.0 |
| | Isostearylglyeerin | 2.0 |
| | Surface-treated titanium oxide (product 29 of the present invention) | 15.0 |
| | Surface-treated iron oxide (product 30 of the present invention) | 2.0 |
| C | Carbomer 4% aqueous solution | 2.5 |
| | pH adjuster | Adequate level |
| | Fragrance | Adequate amount |
| | Antiseptic | Adequate amount |

(Preparation method) Phase B was added to phase A gradually with a homo mixer for emulsification. Phase C was added to phase A,B with a paddle mixer for adjusting the viscosity.

(Results) A preparation excellent in dispersibility, water repellency, and oil repellency was obtained.

Example 11

Lipstick

1. Production Method (Method 27 for Producing Treated Powder)

Titanium oxide (100 g) was weighed and added to a beaker, 100 g of purified water was added, and then the mixture was stirred well. Sodium hydroxide was added to the mixture to adjust to pH 10, 2 g of FOMBLIN HC/P2-1000 was added, and then the resultant was mixed for 30 minutes. FOMBLIN HC/PU-AN5E (1 g) was further added and then the resultant was mixed for 30 minutes. Hydrochloric acid was added to adjust to pH 4.5, and then 1 g of FOMBLIN HC/PU-CAT5 was added. After 30 minutes of stirring, fluid was filtered out. Amino silicone (1 g) was added. The resultant was pulverized with a Henschel mixer and then heated at 130° C. The resultant was designated as product 31 of the present invention.

(Method 28 for Producing Treated Powder)

Iron oxide (100 g) was weighed and added to a beaker, 100 g of purified water was added, and then the mixture was stirred well. Sodium hydroxide was added to the mixture to adjust to pH 10, 2 g of FOMBLIN HC/P2-1000 was added, and then the resultant was mixed for 30 minutes. FOMBLIN HC/PU-AN5E (1 g) was further added and then the resultant was mixed for 30 minutes. Hydrochloric acid was added to adjust to pH 4.5, and then 1 g of FOMBLIN HC/PU-CAT5 was added. After 30 minutes of stirring, fluid was filtered out. Amino silicone (1 g) was added. The resultant was pulverized with a Henschel mixer and then heated at 130° C. The resultant was designated as product 32 of the present invention.

(Method 29 for Producing Treated Powder)

Mica (100 g) was weighed and added to a beaker, 100 g of purified water was added, and then the mixture was stirred well. Sodium hydroxide was added to the mixture to adjust to pH 10, 2 g of FOMBLIN HC/P2-1000 was added, and then the resultant was mixed for 30 minutes. FOMBLIN HC/PU-AN5E (1 g) was further added and then the resultant was mixed for 30 minutes. Hydrochloric acid was added to adjust to pH 4.5, and then 1 g of FOMBLIN HC/PU-CAT5 was added. After 30 minutes of stirring, fluid was filtered out. Amino silicone (1 g) was added. The resultant was pulverized with a Henschel mixer and then heated at 130° C. The resultant was designated as product 33 of the present invention.

2. Formulation

| | |
|---|---|
| Polybutene | 60 |
| Isostearyl malate | 10 |
| Trioctanoin | 10 |
| Dextrin palmitate | 3 |
| Diglycerol triisostearate | 3 |
| Pentaerythrityl tetraisostearate | 3 |
| (Dimethicone/methicone) copolymer | 2 |
| Dimethicone | 2 |
| Calcium carbonate | 1 |
| Dextrin myristate | 1 |
| Surface-treated titanium oxide (product 31 of the present invention) | 1 |
| Surface-treated iron oxide (product 32 of the present invention) | 1 |
| Surface-treated mica (product 33 of the present invention) | 1 |
| Other color materials and fragrances | Remainder (% by mass) |

(Preparation method) With the formulation, a product was produced by uniformly adding and mixing ingredients using a roll mill.

(Results) A lipstick having good dispersibility of pigments and vivid color tone was obtained. Specifically, the lipstick was excellent in adhesiveness and did not easily result in color transfer to a vessel or the like.

All publications, patents, and patent applications cited in this specification are herein incorporated by reference in their entirety.

What is claimed is:

1. A surface-treated powder, wherein the surface of a powder is treated to provide the powder with a coating being a combination of perfluoropolyetherphosphate represented by general formula (1), and a polymer selected from the group consisting of an anionic polymer having a perfluoropolyether chain, which is represented by general formula (2), and a cationic polymer having a perfluoropolyether chain, which is represented by general formula (3):

Chemical formula 1

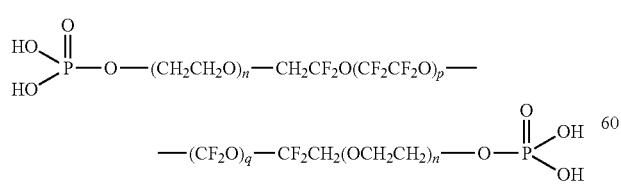

wherein p denotes an integer between 1 and 50, q denotes an integer between 1 and 10, and n denotes an integer between 1 and 5;

Chemical formula 2

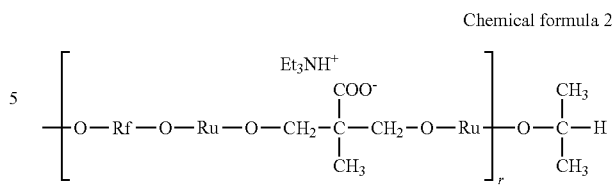

wherein r denotes an integer between 1 and 50, Rf denotes general formula (4), and Ru denotes general formula (5);

Chemical formula 3

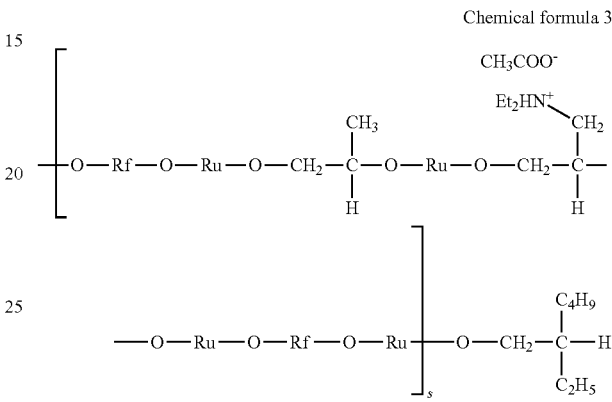

wherein s denotes an integer between 1 and 50, Rf denotes general formula (4), and Ru denotes general formula (5);

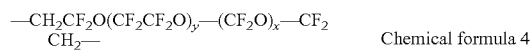

Chemical formula 4 wherein x denotes an integer between 1 and 100 and y denotes an integer between 1 and 100; and Chemical formula 5

wherein A is a functional group in cyclohexane, two of As are —NH—CO— or —CH$_2$—NH—CO—forming a urethane bond structure and two As are the same or different, and the other As denote arbitrarily hydrogens or methyl groups.

2. The surface-treated powder according to claim 1, wherein a total coating amount deposited on the treated powder ranges from 0.5 parts by mass to 40 parts by mass per 100 parts by mass of the material powder.

3. The surface-treated powder according to claim 1, wherein the powder is:
an inorganic pigment selected from the group consisting of iron oxide, zinc oxide, titanium oxide, cerium oxide, magnesium oxide, zirconium oxide, barium sulfate, chromium oxide, ultramarine blue, iron oxide red, magnesium carbonate, calcium carbonate, mica, sericite, talc, silica, kaolin, chromium hydroxide, zinc oxide, carbon black, alumina, aluminium silicate, magnesium silicate, boron nitride, silica-alumina powder, bentonite, and smectite;
an organic powder selected from the group consisting of nylon powder, polyurethane powder, polymethyl methacrylate, styrene-divinylbenzene copolymer, polyethylene powder, silicone resin, Teflon (trademark) powder, silicone gum, silk powder, carnauba wax, rice wax, starch, and microcrystalline cellulose; rhodamine B;
   zirconium selected from the group consisting of red No. 201, black No. 401, yellow No. 4, and blue No. 1;
   an organic colorant that is barium or aluminum lake;
   titanated mica; or
   iron oxide-coated mica.

4. A method for treating the surface of a powder, comprising:
   treating the surface of the powder with perfluoropolyetherphosphate represented by general formula (1), wherein A is a functional group in cyclohexane, two of As are —NH—CO— or —CH$_2$—NH—CO— forming a urethane bond structure and two As are the same or different, and the other As denote arbitrarily hydrogens or methyl groups.

5. The method for treating the surface of a powder for cosmetics according to claim 4, wherein the powder is:
   an inorganic pigment selected from the group consisting of iron oxide, zinc oxide, titanium oxide, cerium oxide, magnesium oxide, zirconium oxide, barium sulfate, chromium oxide, ultramarine blue, iron oxide red, magnesium carbonate, calcium carbonate, mica, sericite, talc, silica, kaolin, chromium hydroxide, zinc oxide, Chemical formula 1

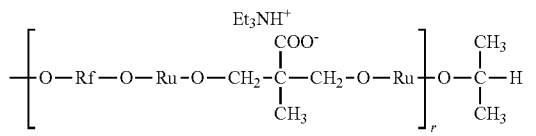

wherein p denotes an integer between 1 and 50, q denotes an integer between 1 and 10, and n denotes an integer between 1 and 5, and an anionic polymer having a perfluoropolyether chain, which is represented by general formula (2), under alkaline conditions of pH8.0 or more, Chemical formula 2

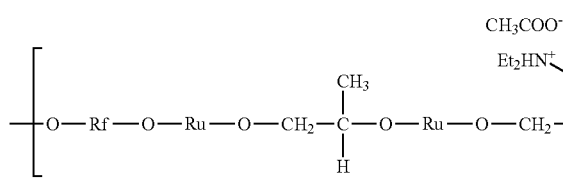

wherein r denotes an integer between 1 and 50, Rf denotes general formula (4), and Ru denotes general formula (5); and, treating the surface of the powder with a cationic polymer having a perfluoropolyether chain, which is represented by general formula (3), under acidic conditions of pH 6.0 or less, carbon black, alumina, aluminium silicate, magnesium silicate, boron nitride, silica-alumina powder, bentonite, and smectite;
   an organic powder selected from the group consisting of nylon powder, polyurethane powder, polymethyl methacrylate, styrene-divinylbenzene copolymer, polyethylene powder, silicone resin, Teflon (trademark) powder, silicone gum, silk powder, carnauba wax, rice wax, starch, and microcrystalline cellulose;
rhodamine B;
   zirconium selected from the group consisting of red No. 201, black No. 401, yellow No. 4, and blue No. 1;
   an organic colorant that is barium or aluminum lake;
   titanated mica; or
   iron oxide-coated mica.

6. The method for treating the surface of a powder according to claim 4, wherein the powder is treated in advance with a surface treatment aid.

Chemical formula 3

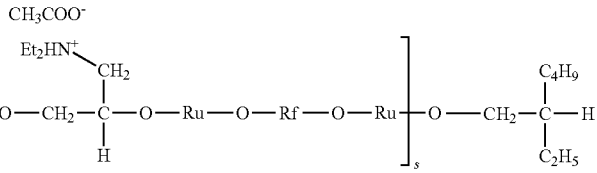

wherein s denotes an integer between 1 and 50, Rf denotes general formula (4), and Ru denotes general formula (5), —CH$_2$CF$_2$O(CF$_2$CF$_2$O)$_y$—(CF$_2$O)$_x$—CF$_2$CH$_2$—   Chemical formula 4 wherein x denotes an integer between 1 and 100 and y denotes an integer between 1 and 100; and Chemical formula 5

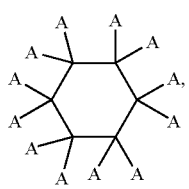

7. The method for treating the surface of a powder according to claim 6, wherein the surface treatment aid is selected from the group consisting of iron chloride, aluminium chloride, aluminium chloride hexahydrate, aluminium hydroxide, aluminium silicate, and aluminium phosphate.

8. Cosmetics, comprising the surface-treated powder according to claim 1.

9. Cosmetics, comprising surface-treated powder, having a coating of a combination of perfluoropolyetherphosphate represented by general formula (1), and a polymer selected from the group consisting of an anionic polymer having a perfluoropolyether chain, which is represented by general formula (2), and a cationic polymer having a perfluoropolyether chain, which is represented by general formula (3):

Chemical formula 1

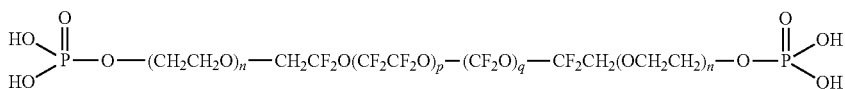

wherein p denotes an integer between 1 and 50, q denotes an integer between 1 and 10, and n denotes an integer between 1 and 5;

Chemical formula 2

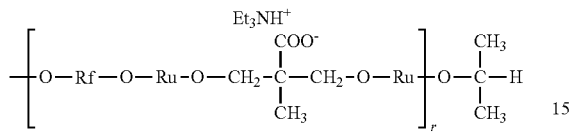

wherein r denotes an integer between 1 and 50, Rf denotes general formula (4), and Ru denotes general formula (5);

Chemical formula 3

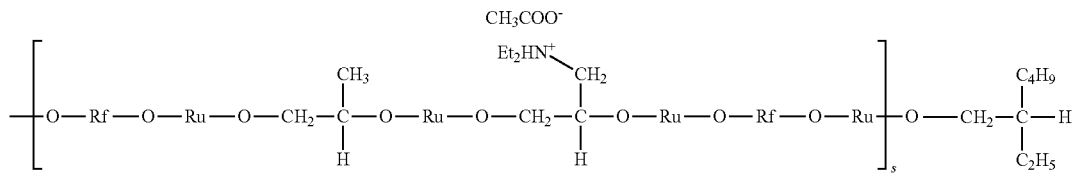

wherein s denotes an integer between 1 and 50, Rf denotes general formula (4), and Ru denotes general formula (5);

—$CH_2CF_2O(CF_2CF_2O)_y$—$(CF_2O)_x$—$_{CF2}CH_2$— Chemical formula 4 wherein x denotes an integer between 1 and 100 and y denotes an integer between 1 and 100; and Chemical formula 5

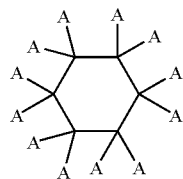

wherein A is a functional group in cyclohexane, two of As are —NH—CO— or —$CH_2$—NH—CO—forming a urethane bond structure and two As are the same or different, and the other As denote arbitrarily hydrogens or methyl groups; obtained by the production method according to claim 4.

* * * * *